United States Patent
Bar Shalom

(10) Patent No.: US 9,226,805 B2
(45) Date of Patent: Jan. 5, 2016

(54) MULTI-POSITION ABUTMENT WITH ANGULAR BALL ATTACHMENT FOR DENTAL IMPLANTS

(75) Inventor: Eliezer Bar Shalom, Nir Galim (IL)

(73) Assignee: Eliezer Bar Shalom, Nir-Galim (IL)

( * ) Notice: Subject to any disclaimer, the term of this patent is extended or adjusted under 35 U.S.C. 154(b) by 462 days.

(21) Appl. No.: 12/470,117

(22) Filed: May 21, 2009

(65) Prior Publication Data

US 2009/0246734 A1 Oct. 1, 2009

Related U.S. Application Data

(63) Continuation of application No. PCT/IL2007/001448, filed on Nov. 22, 2007.

(60) Provisional application No. 60/860,502, filed on Nov. 22, 2006.

(51) Int. Cl.
*A61C 8/00* (2006.01)

(52) U.S. Cl.
CPC ............... *A61C 8/005* (2013.01); *A61C 8/0053* (2013.01); *A61C 8/0066* (2013.01); *A61C 8/0069* (2013.01); *A61C 8/006* (2013.01); *A61C 8/0054* (2013.01); *A61C 8/0068* (2013.01)

(58) Field of Classification Search
CPC .... A61C 8/005; A61C 8/0068; A61C 8/0069; A61C 8/0048; A61C 8/006; A61C 13/225; A61C 13/2656; A61C 8/0018; A61C 8/00; A61C 8/0066; A61C 8/0075; A61C 5/08; B25B 23/00

USPC ................ 433/173, 174, 172, 214, 181, 182, 433/201.1, 215, 74

See application file for complete search history.

(56) References Cited

U.S. PATENT DOCUMENTS

| 4,449,934 | A | * | 5/1984 | Salam | 433/143 |
| 4,823,601 | A | | 4/1989 | Barna | |
| 4,988,297 | A | | 1/1991 | Lazzara | |
| 5,071,350 | A | | 12/1991 | Niznick | |
| 5,073,110 | A | | 12/1991 | Barbone | |

(Continued)

FOREIGN PATENT DOCUMENTS

| DE | 19903482 | 8/2000 |
| DE | 10009448 | 9/2001 |

(Continued)

OTHER PUBLICATIONS

International Search Report mailed Apr. 6, 2009 for PCT/IL2007/001448.

(Continued)

*Primary Examiner* — Cris L Rodriguez
*Assistant Examiner* — Mirayda A Aponte
(74) *Attorney, Agent, or Firm* — Pearl Cohen Zedek Latzer Baratz LLP

(57) ABSTRACT

The present invention relates to an abutment for securing a dental prosthesis to a dental implant. The multi-member abutment corrects for angular misalignment between the dental prosthesis and implant by way of thirty or greater discrete orientations about a central vertical axis and, an external ball that protrudes from the upper surface of the abutment to externally constrain the prosthesis from the side. Exchangeable members are available for variability in height and offset angle beyond a specified range.

13 Claims, 8 Drawing Sheets

(56) References Cited

U.S. PATENT DOCUMENTS

| | | |
|---|---|---|
| 5,195,891 A | 3/1993 | Sulc |
| 5,281,140 A | 1/1994 | Niznick |
| 5,302,125 A * | 4/1994 | Kownacki et al. ............ 433/172 |
| 5,350,302 A | 9/1994 | Marlin |
| 5,577,912 A | 11/1996 | Prins |
| 5,599,185 A * | 2/1997 | Greenberg .................... 433/173 |
| 5,839,898 A | 11/1998 | Fernandes |
| 6,012,923 A * | 1/2000 | Bassett et al. ................ 433/172 |
| 6,299,447 B1 | 10/2001 | Zuest et al. |
| 6,500,003 B2 | 12/2002 | Nichinonni |
| 6,758,672 B2 * | 7/2004 | Porter et al. .................. 433/173 |
| 7,214,063 B2 | 5/2007 | Cohen |
| 2001/0053512 A1 * | 12/2001 | Nichinonni .................... 433/173 |

FOREIGN PATENT DOCUMENTS

| | | |
|---|---|---|
| EP | 0313222 | 4/1989 |
| EP | 0313222 B2 * | 4/1989 |

OTHER PUBLICATIONS

Written Opinion of the International Searching Authority mailed Apr. 6, 2009 for PCT/IL2007/001448.

* cited by examiner

MULTI-POSITION ABUTMENT WITH ANGULAR BALL ATTACHMENT FOR DENTAL IMPLANTS

CROSS REFERENCE TO RELATED APPLICATION

This application is a Continuation Application of international application number PCT/IL2007/001448, filed Nov. 22, 2007, which in turn claimed the benefit of U.S. Provisional Patent Application 60/860,502, filed Nov. 22, 2006, both of which are incorporated herein by reference in their entirety.

FIELD AND BACKGROUND OF THE INVENTION

The present invention relates to the field of dental implants; more specifically, to an interface between a dental implant which is drilled and permanently fixed into the mandibular or maxillary bone and, a removable device inserted into the mouth by the end-user, such as, but not limited to dentures. The interface is known as an abutment in the field of dentistry, and will be referred to as the "invention" herein. Likewise, the removable device will be referred to as "prosthesis."

Dental implants can be screw-like. Conventional two-piece implants comprise a cone-tip externally threaded at the distal or lower end, and a multi-position interface, such as a hexagonal socket head, at the proximal or upper end. Additionally, the proximal end is internally tapped into and below the hexagon socket. Alternatively, some dental implants may have a protruding feature such as a hexagon or other pattern at its proximal end. All features described thus far are concentric about a single vertical axis.

A hole is bored through the gums into the mandible or maxilla jawbone) by a dental surgeon. The dental implant is then fixed in place with implant specific tools thereby eliminating all degrees of freedom of movement. In most cases, the patient's teeth do not align on the same vertical axis as the dental implant. Consequently, an abutment is used to adapt between the implant's vertical axis and that of the prosthesis. The abutment should correct the angular misalignment between the two vertical axes as described above, and in some cases, it may account for translational misalignment.

A replica mold of the patient's mouth is created to facilitate design of the prosthesis in a laboratory environment. Adjustments must then be made when the prosthesis is installed into the patients' mouth in the dental office. Conventional abutments provide freedom of rotation about one or more axes. The dental surgeon fits the prosthesis to the implant via movement of the abutment to the desired position. The abutment is then fixed in place by way of a lock mechanism.

Anatomy of the human mouth varies widely between different individuals. Similarly, each manufacturer produces a unique variation to the prosthesis and implant design. An ideal abutment not only maximizes positional settings, but can accommodate a variety of prostheses and implants with minimal modification.

Numerous abutment designs describe multi-member assemblies in which the first or upper member mates with the prosthesis and is offset at an angle relative to the vertical axis thereby compensating for angular displacement between prosthesis and implant. The second or lower member mates with the dental implant and may rotate in a discrete number of orientations about the implant's vertical axis. In most cases, six orientations—every 60 degrees—are made available whereby a hexagon extrusion on the second member fits into a hexagon socket on the dental implant.

The patents herein are incorporated by reference in their entirety for all purposes. U.S. Pat. No. 6,299,447 issued to Zuest et al, U.S. Pat. No. 5,350,302 issued to Marlin, U.S. Pat. No. 5,195,891 issued to Sulc, and U.S. Pat. No. 4,988,297 issued to Lazarra et al, illustrate designs in which the upper member possesses a fixed offset angle. If the specific angle is unsuitable for the patient, the member may be exchanged for a matching member with a different offset angle.

Alternatively, abutment designs such as U.S. Pat. No. 7,214,063 issued to Cohen, U.S. Pat. No. 6,500,003 issued to Nichinormi, U.S. Pat. No. 5,073,110 issued to Barbone and U.S. Pat. No. 5,071,350 issued to Niznick, employ a spherical or ball-and-socket joint which provides greater flexibility in positioning. These offer freedom of rotation about all three axes: yaw, pitch and roll. The ideal orientation is obtained by unconstrained manipulation of the sphere which is then locked in place. Similarly, U.S. Pat. No. 4,823,601 issued to Linden engages a spherical unit set into a conical receptor.

All abutments disclosed herein are uniformly coupled to the prostheses whereby an extension of the prosthesis inserts into a hollow cylindrical or conical receptor on the proximal or upper aspect of the abutment.

SUMMARY OF THE INVENTION

It is thus the object of the present invention to provide an abutment with thirty or more discrete, repeatable and stable in-plane orientations about the vertical axis. Moreover, the abutment will grasp the prosthetic by a unique external ball mechanism which inherently accommodates the angular misalignment between the patient's teeth and dental implant. Said invention is designed to adapt to conventional dental implants with a hexagonal socket head and a multitude of prostheses including but not limited to dentures.

The present invention comprises two or more members. One member interfaces with the prosthetic by way of an external ball offset at an angle, and a second member provides variability in orientation about the vertical axis and inserts into the dental implant. A third member may clamp the preceding two members together and is anchored deep within the dental implant. The first member has several interchangeable versions with varying offset angles for the external ball, while the second member has several interchangeable versions with varying height. The external ball feature of the first member applies force on the prosthesis from the external or gingival side of the teeth in single point contact. The external hexagon on the distal or lower face of the second member fits into the hexagon socket head of a conventional dental implant. This feature enables orientation for example in six different positions about the vertical axis. The mating hexagon geometries at the interface between abutment and implant constrain freedom of movement in both translation and rotation about the vertical axis, thereby imparting stability to the interface between prosthesis and dental implant.

By one embodiment, the first member contains a positive semi-spherical element protruding from the distal or lower face. This feature mates with one of several spherical concave divots on the proximal or upper face of the second member, equidistant from and spaced about the vertical axis. This assembly enables additional orientations about the vertical axis. Once the two members have been clamped together, the spherical geometry constrains any planar movement, thereby imparting stability to the structure. Integration with the hexagon may yield for example, a total of thirty orientations.

In another embodiment, the first member features a positive semi-spherical element as described above, or a positive wedge-like element protruding from the distal or lower face and radiating from the central vertical axis toward the member perimeter. This feature mates with one of several complementary wedges milled into the proximal or upper face of the second member, radiating from the central vertical axis toward the member perimeter. This assembly may also yield for example, a total of thirty stable orientations.

In a third embodiment, the first member features a multi-sided polygon on its distal or lower face that mates with a complementary multi-sided polygon on the proximal or upper face of the second member. This feature alone enables multiple orientations about the vertical axis. Once again, the natural geometry of the mating polygons eliminates freedom of translation or rotation at both interfaces.

BRIEF DESCRIPTION OF THE DRAWINGS

The subject matter regarded as the invention will become more clearly understood in light of the ensuing description of embodiments thereof, given by way of example only, with reference to the accompanying figures, wherein.

DESCRIPTION OF SOME EMBODIMENTS OF THE INVENTION

Figure 1A:
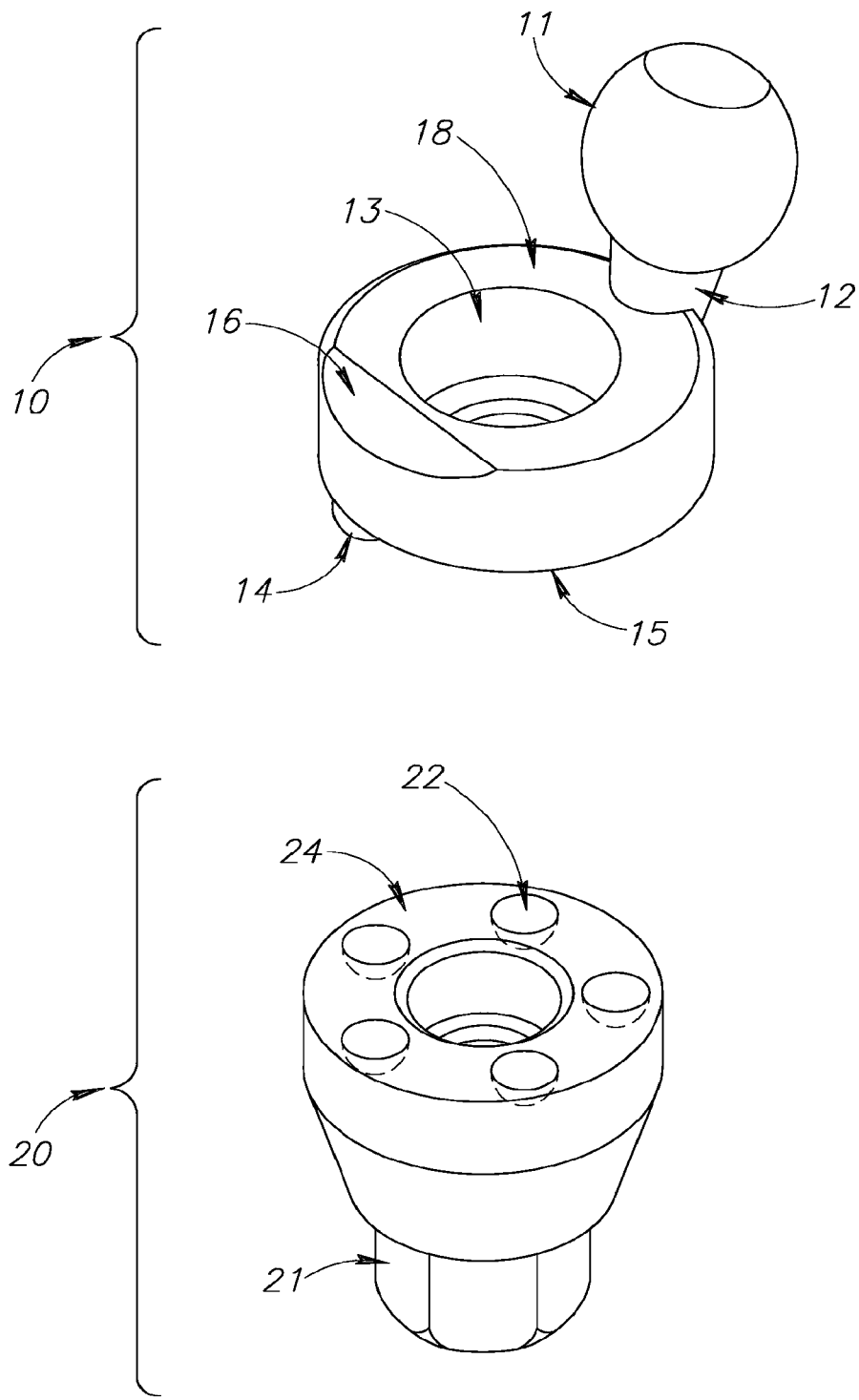
FIG. 1a presents a side perspective exploded view of one embodiment of the two-member abutment in which the first member is characterized by a semi-spherical element protruding from the lower or distal face, and the second member is characterized by five spherical concave divots on the proximal or upper face.
Figure 1B:
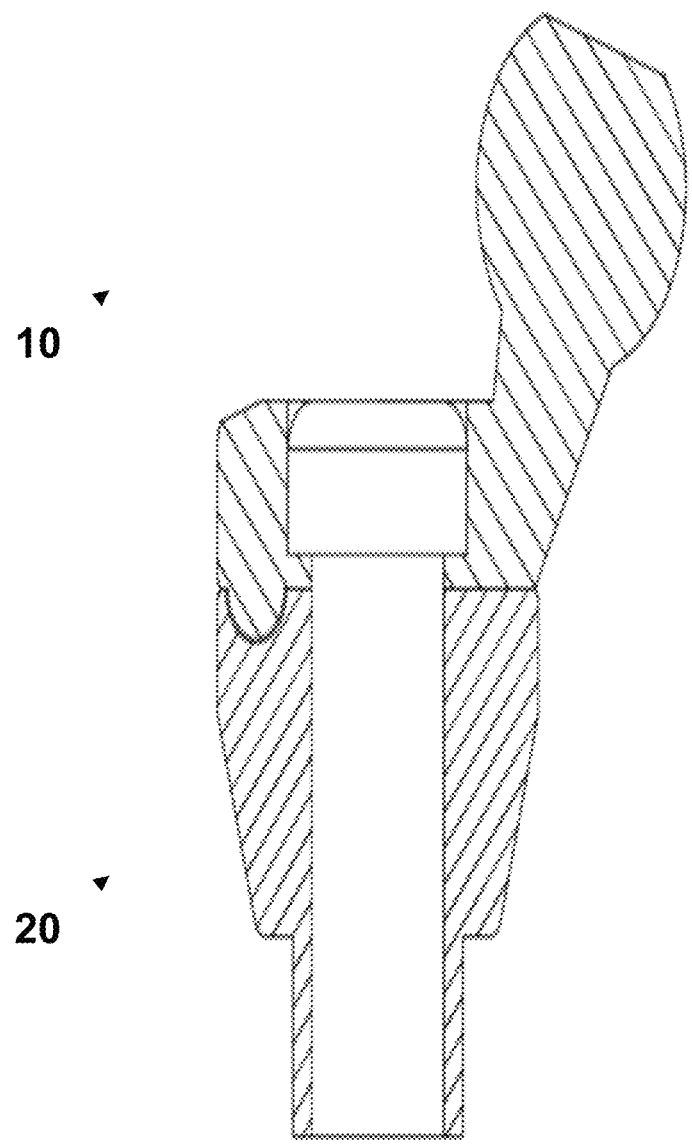
FIG. 1b presents a cross-section view of the two-member abutment in which the first member is characterized by a semi-spherical element protruding from the lower or distal face, and the second member is characterized by five spherical divots on the proximal or upper face.
Figure 2:
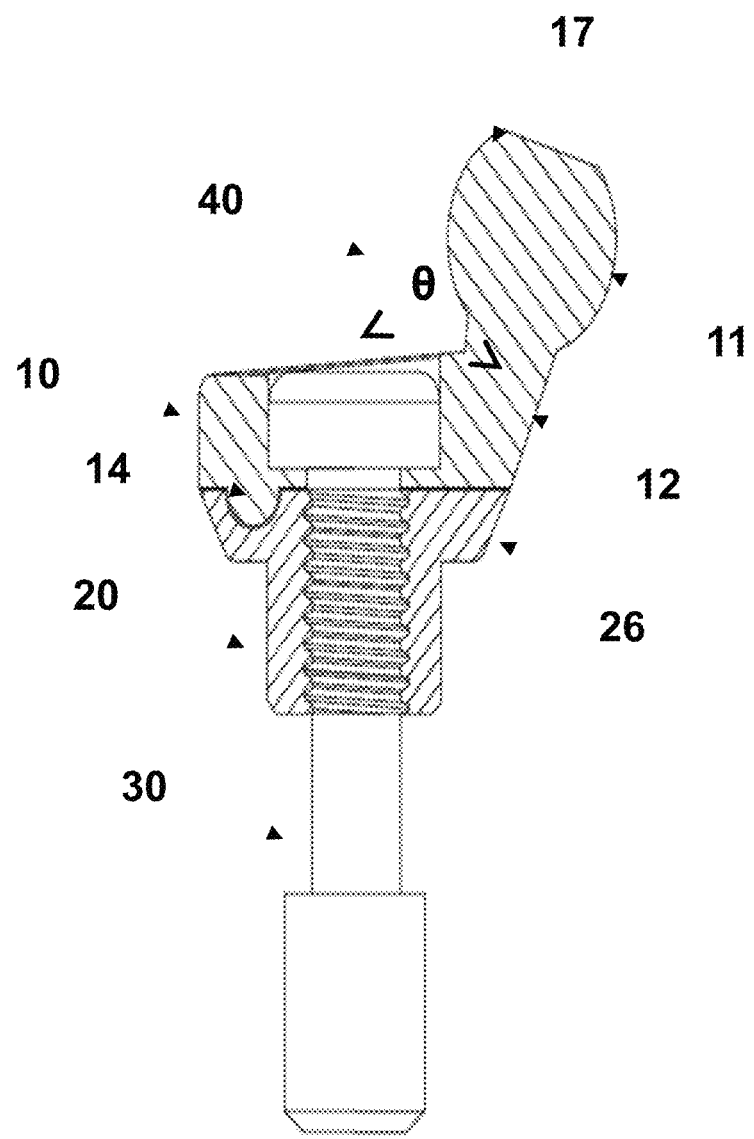
FIG. 2 presents a cross-section view of the two-member abutment in which the first member and second member are clamped together by a screw.

As illustrated in FIGS. 1-2, one embodiment of the present abutment invention contains the first member 10 that mates with a second member 20. These may be clamped together with a fixation screw 30 that threads into the dental implant as detailed in FIG. 2. The enlarged head of the fixation screw 30 drops into a vertical countersink 13 of first member 10 with a clearance fit, and is threaded through a tapped hole in the second member 20. The angular ball 11 of the first member 10 extends from an arm 12 on the upper 18 and side surfaces of the first member 10 at angle theta relative to the reference vertical axis 40. This angle may be collinear with the chamfer 26 of second member 20. The angle theta is selected to constrain movement of the prosthesis, whose vertical axis may be at an angular offset from the vertical axis 40. The angular ball 11 will be in contact with a single point on the external aspect of prosthesis. The angular ball 11 also contains a flattened surface 17 at its top which may be perpendicular to theta. The horizontal upper surface 18 of first member 10 is chamfered 16 at a non-specific angle on the side opposite to the abutment from the angular ball 11 in order to reduce material bulk of the abutment on the internal or lingual side of the prosthesis. Semi-spherical protrusion 14 emanates from the lower face 15 of first member 10 and will mate with a complementary feature on second member 20. The nature of this assembly imparts geometric stability at the interface between members 10 and 20.

Figure 3A:
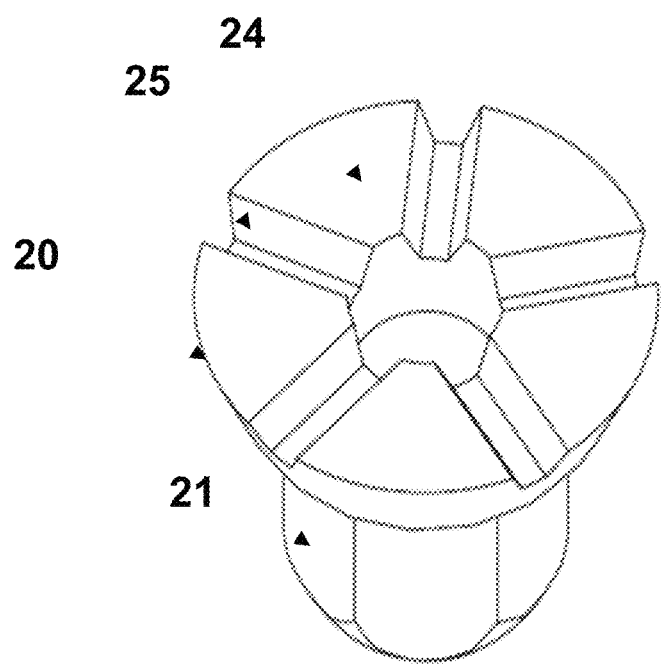
FIG. 3a presents a side perspective view of one embodiment of the second member with five concave divots.

FIG. 3a illustrates one embodiment of the second member. The upper surface 24 is horizontal, into which for example, five concave divots 22 are recessed. The lower portion of second member 20 is characterized by an external hexagonal pattern 21 that will form a perfect fit with the hexagon socket in relevant dental implant designs.

Figure 3B:
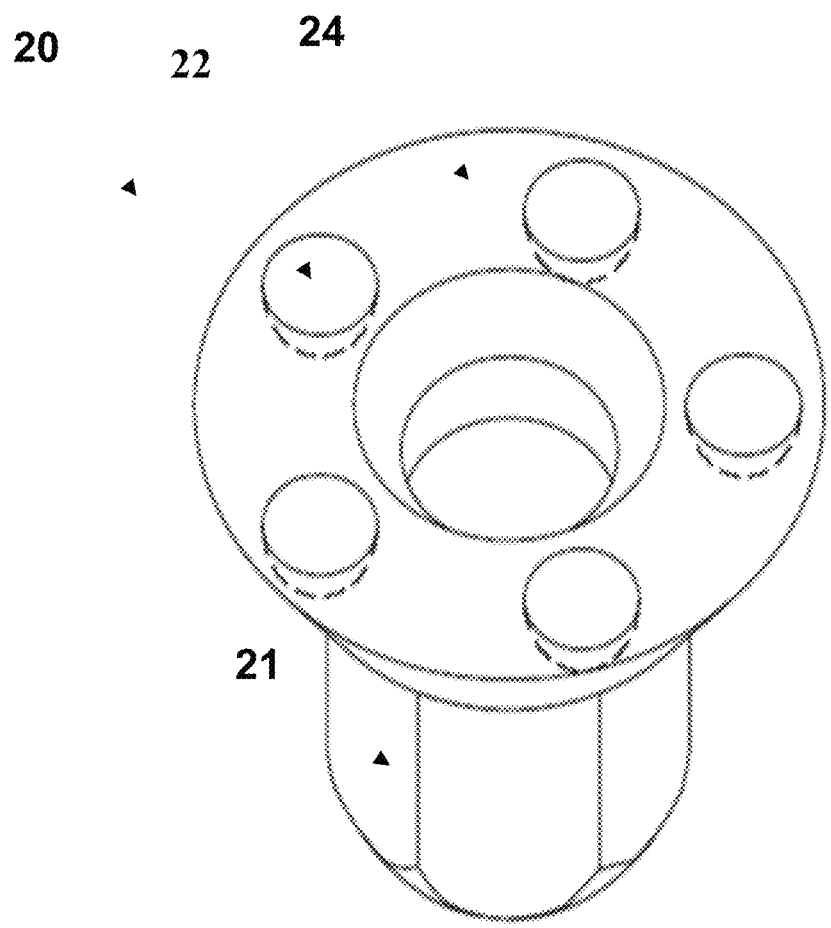
FIG. 3b presents a side perspective view of one embodiment of the second member with five radial grooves.

FIG. 3b illustrates another embodiment of the second member. The upper surface 24 is horizontal, into which for example, five grooves 25 are milled. The lower portion of second member 20 is characterized by an external hexagonal pattern 21 that will form a perfect fit with the hexagon socket in relevant dental implant designs.

Figure 3C:
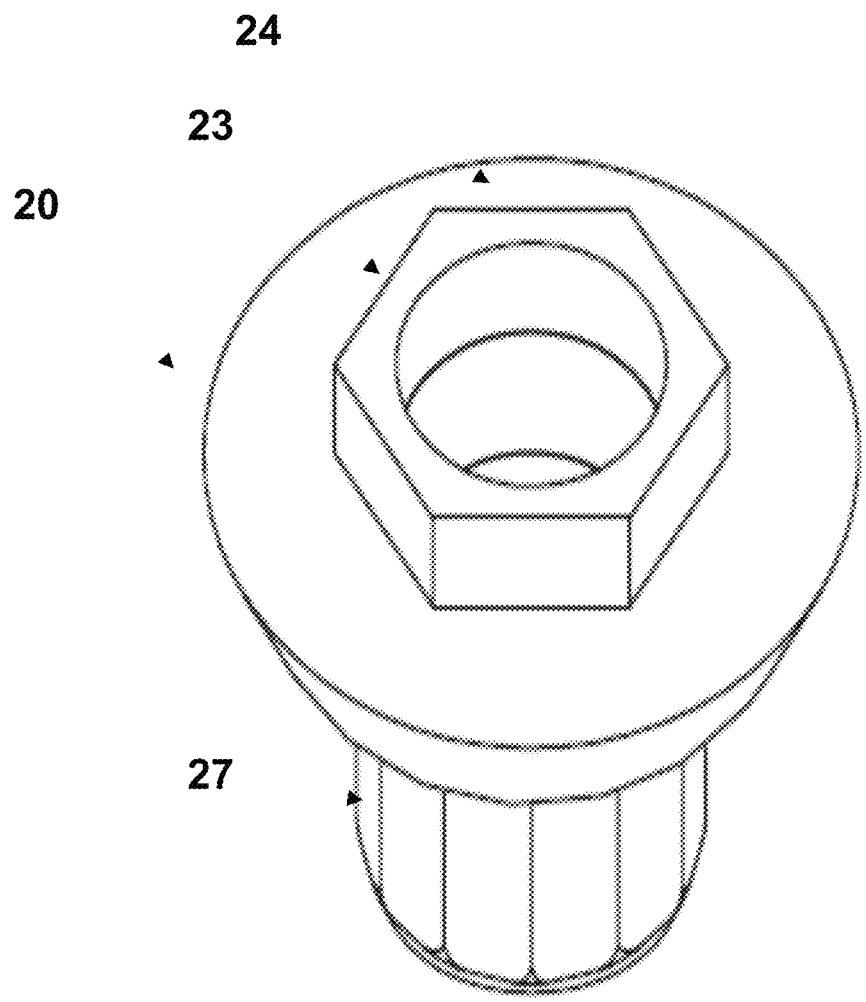
FIG. 3c presents a side perspective view of one embodiment of the second member with multi-sided polygons on both upper and lower faces.

FIG. 3c illustrates yet another embodiment of the second member. In this abutment assembly, the proximal or upper surface 24 is horizontal, from which a multi-sided polygon protrusion 23 emanates. The upper polygon protrusion will mate with a multi-sided polygon socket on the lower or distal face of a complementary embodiment of the first member. The lower portion of second member 20 is characterized by an external multi-sided polygon pattern 27 that will mate with the multi-sided polygon socket in relevant dental implant designs.

Figure 4A:
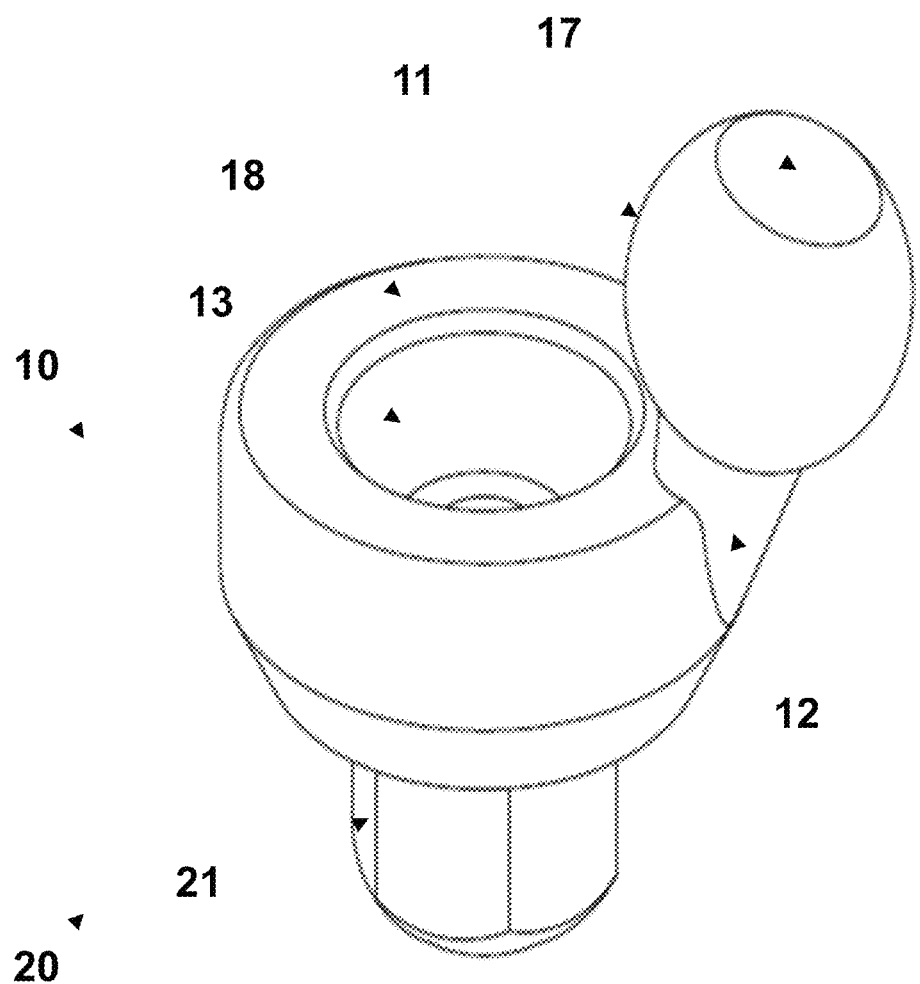
FIG. 4a presents a side perspective view of one embodiment of the assembled two-member abutment.

FIG. 4a provides an additional perspective of the two-member abutment.

Figure 4B:
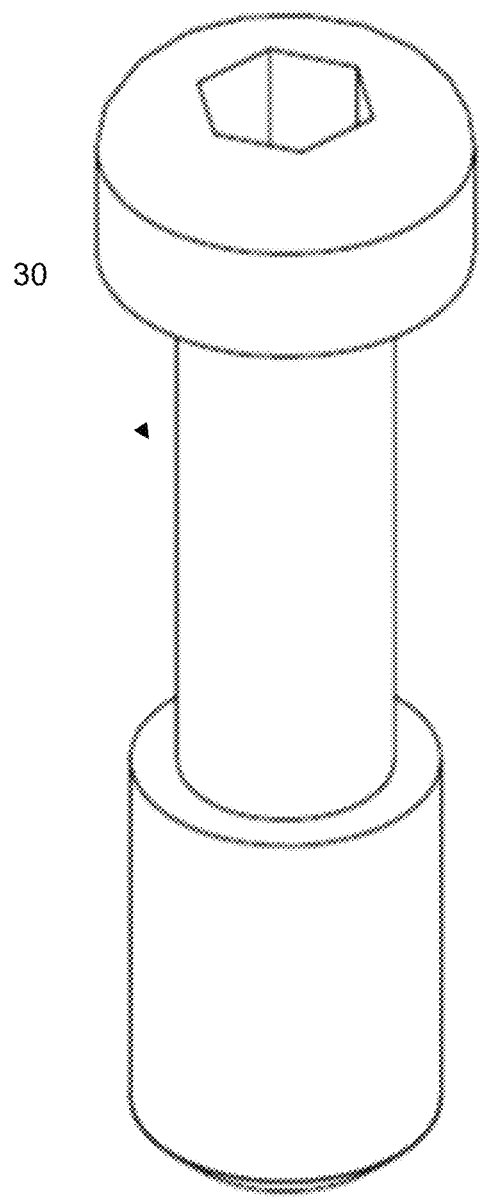
FIG. 4b presents a side perspective view of a sample fixation screw.

FIG. 4b provides an additional perspective of the fixation screw.

An embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "one embodiment", "an embodiment", "some embodiments" or "other embodiments" means that a particular feature, structure, or characteristic described in connection with the embodiments is included in at least one embodiment, but not necessarily all embodiments, of the inventions.

It is understood that the phraseology and terminology employed herein is not to be construed as limiting and is for descriptive purpose only.

The principles and uses of the teachings of the present invention may be better understood with reference to the accompanying description, figures and examples.

It is to be understood that the details set forth herein do not construe a limitation to an application of the invention. Furthermore, it is to be understood that the invention can be carried out or practiced in various ways and that the invention can be implemented in embodiments other than the ones outlined in the description below.

It is to be understood that the terms "including", "comprising", "consisting" and grammatical variants thereof do not preclude the addition of one or more members, features, steps, integers or groups thereof and that the terms are not to be construed as specifying members, features, steps or integers.

The phrases "consisting essentially of", and grammatical variations thereof, when used herein are not to be construed as excluding additional members, steps, features, integers or groups thereof but rather that the additional features, integers, steps, members or groups thereof do not materially alter the basic and novel characteristics of the claimed composition, device or method.

If the specification or claims refer to "an additional" element, that does not preclude there being more than one of the additional element.

It is to be understood that where the claims or specification refer to "a" or "an" element, such reference is not to be construed as there being only one of that element.

It is to be understood that where the specification states that a member, feature, structure, or characteristic "may", "might", "can" or "could" be included, that particular member, feature, structure, or characteristic is not required to be included.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention can be implemented in the testing or practice with methods and materials equivalent or similar to those described herein.

The terms "bottom", "below", "top" and "above" as used herein do not necessarily indicate that a "bottom" member is below a "top" member, or that a member that is "below" is indeed "below" another member or that a member that is "above" is indeed "above" another member. As such, directions, members or both may be flipped, rotated, moved in space, placed in a diagonal orientation or position, placed horizontally or vertically, or similarly modified. Accordingly, it will be appreciated that the terms "bottom", "below", "top" and "above" may be used herein for exemplary purposes only, to illustrate the relative positioning or placement of certain members, to indicate a first and a second member or to do both.

While the invention has been described with respect to a limited number of embodiments, these should not be construed as limitations on the scope of the invention, but rather as exemplifications of some of the preferred embodiments. Those skilled in the art will envision other possible variations, modifications, and applications that are also within the scope of the invention. Accordingly, the scope of the invention should not be limited by what has thus far been described, but by the appended claims and their legal equivalents.

What is claimed is:

1. An abutment for connecting a prosthesis to a dental implant in a stable manner that provides multiple discrete orientations about a vertical axis of the dental implant and compensates for angular misalignment between said prosthesis and said dental implant comprising:
    a member having the same vertical axis as the dental implant, attachable distally to the prosthesis whose vertical axis is at an angular offset from the vertical axis of the member, the member comprising distally a semi-spherical element extending from and surrounding a top of an angular arm integral with the member, the angular arm and the semi-spherical element extending beyond the circumference of an upper surface of the member from which the angular arm extends and distally from the vertical axis and inclined at an angle relative to the vertical axis and away from the vertical axis, the semi-spherical element arranged to contact the prosthesis at a single external point of contact on the prosthesis at one end, at an angle relative to the vertical axis of the dental implant, and the member is arranged to be attached to the dental implant at a lower surface of the member, the lower surface having a chamfer around its periphery and the angular arm is collinear with the chamfer of the lower surface, wherein said member can rotate about said vertical axis of the member relative to the dental implant, thus providing multiple discrete orientations about the vertical axis of the member;
    wherein said semi-spherical element externally constrains said prosthesis by imposing a force on the single external point of contact and simultaneously adjusts for angular misalignment, wherein said providing multiple discrete orientations enables defining the angular position of said semi-spherical element; and
    a fixation element to be anchored within the dental implant and to clamp said member into the dental implant,
    wherein geometry of the abutment imparts stability to an interface between said prosthesis and said dental implant.

2. The abutment of claim 1, wherein:
the member further comprises:
    a first member having the same vertical axis as the dental implant, attachable distally to the prosthesis whose vertical axis is at an angular offset from the vertical axis of the first member, the first member comprising distally said semi-spherical element extending from and surrounding a top of said angular arm which is at an angular offset from the vertical axis of the first member, the semi-spherical element arranged to contact the prosthesis at a single external point of contact on the prosthesis at an angle relative to the vertical axis of the dental implant; and
    a second member having the same vertical axis as the dental implant and a horizontal upper surface and a lower surface having a chamfer around its periphery, and is arranged to be attached to the first member at on the upper surface of the second member, and to the dental implant at the lower surface of the second member, wherein said second member can rotate about said vertical axis of the second member relative to both said dental implant and first member, thus providing multiple discrete orientations about said vertical axis of the second member, wherein the semi-spherical element extending from said angular arm is connected to said first member, wherein said angular arm is at an angular offset from said vertical axis of the first member, wherein said semi-spherical element externally constrains said prosthesis by imposing a force on a single contact point and simultaneously adjusts for angular misalignment, wherein said providing multiple discrete orientations enables defining the angular position of said semi-spherical element, wherein the angular arm is collinear with the chamfer of the second member; and
the fixation element is arranged to be anchored within the dental implant and to clamp said first and second members together,
wherein geometry of the abutment imparts stability to an interface between said prosthesis and said dental implant, and wherein the abutment comprises a set of complementary mating mechanisms between said first and second members that connect the first and the second members at a user selected angle while allowing their exact and stiff connection.

3. The abutment of claim 2, wherein said second member comprises a polygonal adaptor configured to interface with a corresponding polygonal socket of the dental implant, in order to obtain multiple discrete orientations about a vertical axis of said implant and said second member.

4. The abutment of claim 2, wherein the set of complementary mating mechanisms between said first and second members comprises a wedge-groove combination in order to obtain additional discrete rotational orientations about the vertical axis of the second member.

5. The abutment of claim 1, wherein the set of complementary mating mechanisms between said first and second members comprises a polygon extrusion-socket combination in order to obtain additional discrete rotational orientations about the vertical axis of the second member.

6. An abutment for connecting a prosthesis to a dental implant in a stable manner that provides multiple discrete orientations about a vertical axis of the dental implant and compensates for angular misalignment between said prosthesis and said dental implant comprising:
- a first member having the same vertical axis as the dental implant, attachable distally to the prosthesis whose vertical axis is at an angular offset from the vertical axis of the first member, the first member comprising distally a semi-spherical element extending from and surrounding a top of an angular arm integral with the first member, the angular arm and the semi-spherical element extending beyond the circumference of an upper surface of the first member from which the angular arm extends and distally from the vertical axis and inclined at an angle relative to the vertical axis and away from the vertical axis, the semi-spherical element arranged to contact the prosthesis at a single external point of contact on the prosthesis at an angular offset relative to the vertical axis of the dental implant;
- a second member having the same vertical axis as the dental implant and a horizontal upper surface and a lower surface having a chamfer around its periphery, and is arranged to be attached to the first member at on the upper surface of the second member, and to the dental implant at the lower surface of the second member, wherein said second member can rotate about said vertical axis of the second member relative to both said dental implant and first member, thus providing multiple discrete orientations about said vertical axis of the second member, wherein the angular arm is collinear with the chamfer of the second member;
- wherein said semi-spherical element externally constrains said prosthesis by imposing a force on a single contact point and simultaneously adjusts for angular misalignment, wherein said providing multiple discrete orientations enables defining the angular position of said semi-spherical element; and
- a fixation element to be anchored within the dental implant and to clamp said first and second members together,
- wherein geometry of the abutment imparts stability to an interface between said prosthesis and said dental implant, and
- wherein the abutment comprises a set of complementary mating mechanisms between said first and second members that connect the first and the second members at a user selected angle while allowing their exact and stiff connection.

7. The abutment of claim 6, wherein the first and second members can be exchanged to accommodate large variations in angular offset and height.

8. The abutment of claim 6, wherein the complementary mating mechanisms comprise said first member further comprising at least one protrusion and said second member further comprising a multiplicity of concave divots aligned at predefined distances from one another, along a surface of said second member, enabling said multiplicity of concave divots to discretely mate with said at least one protrusion,
- wherein the angular position of said first member in relation to said second member is defined by mating of said at least one protrusion with corresponding at least one of said multiplicity of concave divots, wherein once mating of the at least one protrusion with said corresponding at least one of said multiplicity of concave divots is carried out, the abutment is configured to be clamped to said implant by clamping the fixation element through the first member, the second member and the implant.

9. The abutment of claim 6, wherein said fixation element is a fixation screw enabling the second member to be clamped to the implant by screwing the fixation screw through the implant and the second member.

10. The abutment of claim 6, wherein said semi-spherical element enables connecting to the prosthesis by acting as a snap fastener, enabling said spherical element to interlock with a corresponding groove in the prosthesis.

11. The abutment of claim 6, wherein said semi-spherical element is trimmed at an edge that is to be received by the prosthesis.

12. A system comprising:
- a prosthesis,
- a dental implant having a vertical axis, and
- an abutment for connecting the prosthesis to the dental implant in a stable manner that provides multiple discrete orientations about the vertical axis of the dental implant and compensates for angular misalignment between said prosthesis and said dental implant, the abutment comprising:
  - a member having the same vertical axis as the dental implant, attachable distally to the prosthesis whose vertical axis is at an angular offset from the vertical axis of the member, the member comprising distally a semi-spherical element extending from and surrounding a top of an angular arm integral with the member, the angular arm and the semi-spherical element extending beyond the circumference of an upper surface of the member from which the angular arm extends and distally from the vertical axis and inclined at an angle relative to the vertical axis and away from the vertical axis, the semi-spherical element arranged to contact the prosthesis at a single external point of contact on the prosthesis at one end, at an angle relative to the vertical axis of the dental implant, and the member is arranged to be attached to the dental implant at a lower surface of the member, the lower surface having a chamfer around its periphery and the angular arm is collinear with the chamfer of the lower surface, wherein said member can rotate about said vertical axis of the member relative to the dental implant, thus providing multiple discrete orientations about the vertical axis of the member;
  - wherein said semi-spherical element externally constrains said prosthesis by imposing a force on a single contact point and simultaneously adjusts for angular misalignment, wherein said providing multiple discrete orientations enables defining the angular position of said semi-spherical element; and a fixation element to be anchored within the dental implant and to clamp said member into the dental implant, wherein geometry of the abutment imparts stability to an interface between said prosthesis and said dental implant.

13. The system of claim 12, wherein the member comprises:

a first member having the same vertical axis as the dental implant, attachable distally to the prosthesis whose vertical axis is at an angular offset from the vertical axis of the first member, the first member comprising distally said semi-spherical element extending from and surrounding a top of said angular arm which is at an angular offset from the vertical axis of the first member, the semi-spherical element arranged to contact the prosthesis at a single external point of contact on the prosthesis at an angle relative to the vertical axis of the dental implant; and a second member having the same vertical axis as the dental implant and a horizontal upper surface and a lower surface having a chamfer around its periphery, and is arranged to be attached to the first member on the upper surface of the second member, and to the dental implant at the lower surface of the second member, wherein said second member can rotate about said vertical axis of the second member relative to both said dental implant and first member, thus providing multiple discrete orientations about the vertical axis of the second member, wherein the semi-spherical element extending from said angular arm is connected to said first member, wherein said angular arm is at an angular offset from said vertical axis of the first member, wherein said semi-spherical element externally constrains said prosthesis by imposing a force on a single contact point and simultaneously adjusts for angular misalignment, wherein said providing multiple discrete orientations enables defining the angular position of said semi-spherical element, wherein the angular arm is collinear with the chamfer of the second member; and the fixation element is arranged to be anchored within the dental implant and to clamp said first and second members together, wherein geometry of the abutment imparts stability to an interface between said prosthesis and said dental implant, and wherein the abutment comprises a set of complementary mating mechanisms between said first and second members that connect the first and the second members at a user selected angle while allowing their exact and stiff connection.

* * * * *